US010087382B2

(12) United States Patent
Nordvik et al.

(10) Patent No.: US 10,087,382 B2
(45) Date of Patent: Oct. 2, 2018

(54) FLUID ADDITIVE AND METHOD OF MAKING AND USING THE SAME

(71) Applicants: Schlumberger Norge AS, Stavanger (NO); M-I L.L.C., Houston, TX (US)

(72) Inventors: Tore Nordvik, Sandnes (NO); Anders Grinrod, Sandnes (NO); Rachael Anne Cole, Sandnes (NO); Astrid Lone, Sandnes (NO); Chandrashekhar Yeshwant Khandekar, Katy, TX (US)

(73) Assignees: Schlumberger Norge AS, Stavanger (NO); M-I L.L.C., Houston, TX (US)

( * ) Notice: Subject to any disclaimer, the term of this patent is extended or adjusted under 35 U.S.C. 154(b) by 0 days.

(21) Appl. No.: 14/076,800

(22) Filed: Nov. 11, 2013

(65) Prior Publication Data

US 2015/0128484 A1   May 14, 2015

(51) Int. Cl.
| | |
|---|---|
| *C10L 1/18* | (2006.01) |
| *C10L 1/19* | (2006.01) |
| *C07C 67/08* | (2006.01) |
| *C07C 69/675* | (2006.01) |
| *C07C 69/84* | (2006.01) |
| *C10L 10/04* | (2006.01) |
| *C10L 10/08* | (2006.01) |
| *C08G 83/00* | (2006.01) |
| *C09K 8/524* | (2006.01) |
| *C10L 1/198* | (2006.01) |

(52) U.S. Cl.
CPC ............ *C10L 1/1915* (2013.01); *C07C 67/08* (2013.01); *C07C 69/675* (2013.01); *C07C 69/84* (2013.01); *C08G 83/003* (2013.01); *C09K 8/524* (2013.01); *C10L 1/1986* (2013.01); *C10L 10/04* (2013.01); *C10L 10/08* (2013.01); *C10L 2200/04* (2013.01); *C10L 2230/08* (2013.01)

(58) Field of Classification Search
CPC ....... C07C 67/08; C07C 69/675; C07C 69/84; C08G 83/003; C10L 10/04; C10L 10/08; C10L 1/1915; C10L 2200/04; C10L 2230/08; C10L 1/1986; C09K 8/524
USPC .................. 44/398; 554/1, 229, 161; 585/3; 208/86, 309
See application file for complete search history.

(56) References Cited

U.S. PATENT DOCUMENTS

| | | | |
|---|---|---|---|
| 5,418,301 A | * | 5/1995 | Hult ...................... C08G 63/12 525/437 |
| 2007/0062698 A1 | | 3/2007 | Smith et al. |
| 2008/0032902 A1 | | 2/2008 | Rivers et al. |
| 2008/0153931 A1 | | 6/2008 | Bruchmann et al. |

(Continued)

FOREIGN PATENT DOCUMENTS

| | | | |
|---|---|---|---|
| WO | 2013019704 A1 | 2/2013 | |
| WO | WO 2013019704 A1 | * 2/2013 | ............. C09K 8/035 |

OTHER PUBLICATIONS

Manek, M.B., "Asphaltene Dispersants as Demulsification Aids", SPE 28972—SPE International Symposium on Oilfield Chemistry, San Antonio, Texas, Feb. 14-17, 1995, pp. 1-9.

(Continued)

*Primary Examiner* — Latosha Hines
(74) *Attorney, Agent, or Firm* — David J. Smith

(57) ABSTRACT

A number of variations may include a product including a fluid additive including at least one asphaltene dispersant/inhibitor including a branched dendritic core and at least one carboxylic acid moiety.

17 Claims, 6 Drawing Sheets

(56) References Cited

U.S. PATENT DOCUMENTS

| | | | | |
|---|---|---|---|---|
| 2008/0207871 | A1* | 8/2008 | Seiler | A61K 8/85 |
| | | | | 528/361 |
| 2011/0243884 | A1* | 10/2011 | O'Shea | C07C 69/40 |
| | | | | 424/78.36 |
| 2014/0130581 | A1* | 5/2014 | Ovalles | C09K 8/04 |
| | | | | 73/61.55 |
| 2014/0224495 | A1* | 8/2014 | Khandekar | C09K 8/035 |
| | | | | 166/310 |

OTHER PUBLICATIONS

Tomalia, et al., "Starburst Dendrimers: Molecular-Level Control of Size, Shape, Surface Chemistry, Topology, and Flexibility from Atoms to Macroscopic Matter", Angewandte Chemie International Edition in English, vol. 29 (2), 1990, pp. 138-175.

Hedenqvist et al, "Transport Properties of Hyperbranched and Dendrimer-Like Star Polymers", Polymer vol. 41 (2000), pp. 1827-1840.

International Search Report and Written Opinion from corresponding PCT Application Serial No. PCT/US2014/064744, dated Feb. 23, 2015, 10 pages.

* cited by examiner

| Product Name | % Asphaltene precipitate @Time | | | |
|---|---|---|---|---|
| | 2hrs | 4hrs | 6hrs | 24hrs |
| Blank | 10.0 | 8.5 | 7.0 | 5.0 |
| FlowSolve 110 | 0.0 | 0.0 | 0.0 | 0.1 |
| Example 2a | 0.0 | 0.0 | 0.2 | 0.7 |
| Example 2b | 0.0 | 0.0 | 0.2 | 0.8 |
| Example 2c | 0.0 | 0.0 | 0.2 | 0.8 |
| Example 2d | 0.0 | 0.0 | 0.1 | 0.7 |
| Example 2e | 0.0 | 0.0 | 0.2 | 0.8 |

| Product Name | % Asphaltene precipitate @Time | | | |
|---|---|---|---|---|
| | 2hrs | 4hrs | 6hrs | 24hrs |
| Blank | 10.0 | 8.5 | 6.8 | 4.8 |
| FlowSolve 110 | 0.0 | 0.0 | 0.0 | 0.0 |
| Example 1a | 0.0 | 0.0 | 0.1 | 0.3 |
| Example 1b | 0.0 | 0.0 | 0.1 | 0.3 |
| Example 1c | 0.0 | 0.0 | 0.1 | 0.4 |
| Example 1d | 0.0 | 0.0 | 0.1 | 0.3 |
| Example 1e | 0.0 | 0.0 | 0.1 | 0.3 |

US 10,087,382 B2

FLUID ADDITIVE AND METHOD OF MAKING AND USING THE SAME

TECHNICAL FIELD

The field to which the disclosure generally relates to includes fluids, including, but not limited to hydrocarbon fluids.

BACKGROUND

Currently, some fluids may contain asphaltenes that may aggregate, flocculate, and deposit. It is known in the industry that asphaltenes may be present in produced petroleum products, such as crude oil, and may cause major problems upon deposition. A sudden change in conditions along the production line of the petroleum product can cause asphaltene to precipitate. Depressurization and/or temperature change often lead to destabilization of the petroleum product, hence asphaltenes may flocculate and deposit. The onset of asphaltene deposit is not necessary dependent on the concentration of asphaltenes, and asphaltene aggregation, flocculation, precipitation and deposition mechanisms are still not fully understood.

Asphaltenes are often defined, not by their chemical functionality and structure, but operationally as those species that can precipitate upon the addition of light petroleum ether like n-pentane and n-heptane, while remaining soluble in aromatic solvents like toluene and xylenes. In general, asphaltenes are defined as polydisperse macromolecules consisting of aromatic rings with alkyl groups of varying lengths with the presence of heteroatoms such as nitrogen, oxygen and sulfur. In addition, metals such as nickel, vanadium and iron may be present as well. Asphaltene molecular weight mass is often accepted as between 500 and 1000 Daltons. Moreover, the carbon to hydrogen ratio is different depending on what petroleum product the asphaltene is isolated from, but usually is found to be 1:1.2. In many cases, the most dominant heteroatom is sulfur, with oxygen and nitrogen as minor constituents. Similar structures as asphaltene (i.e. polycyclic molecules with more aliphatic side-chain character, but in a lower molecular weight range) are defined as maltenes, or simply resins. Different from asphaltenes, this resinous component in petroleum product is soluble in heptanes.

Due to the nature of asphaltenes to flocculate and deposit under a variety of environmental conditions, there is a long felt need to discover and develop effective products, methods and processes to disperse and/or inhibit asphaltene flocculation, precipitation, and/or growth in fluids, such need met, at least in part, by the following disclosure.

SUMMARY OF ILLUSTRATIVE VARIATIONS

A number of variations may include a product including a fluid additive comprising at least one asphaltene dispersant/inhibitor comprising a branched dendritic core and at least one carboxylic acid moiety.

A number of variations may include a method including adding an asphaltene dispersant/inhibitor comprising the reaction product of a branched dendritic core and a carboxylic acid to a first fluid to produce a second fluid, wherein the second fluid has a reduced percentage of asphaltene precipitation, flocculation, or deposition.

A number of variations may include a process including providing a branched dendritic core comprising greater than or equal to about 16 terminal hydroxyl groups; providing at least one carboxylic acid moiety comprising from 6 to 40 carbon atoms; and reacting the branched dendritic core with the carboxylic acid moiety to provide an asphaltene dispersant/inhibitor.

A number of variations may include a process including providing a branched dendritic core comprising greater than or equal to about 16 terminal hydroxyl groups; providing at least one carboxylic acid moiety comprising from 6 to 40 carbon atoms; and reacting the branched dendritic core with the carboxylic acid moiety to provide an asphaltene dispersant/inhibitor wherein the step of reacting the branched dendritic core with the carboxylic acid moiety to provide an asphaltene dispersant/inhibitor further comprises reacting the branched dendritic core with the spacer wherein the spacer is esterified with at least one of the terminal hydroxyl groups of the branched dendritic core to produce a hybrid branched dendritic core; and thereafter reacting the hybrid branched dendritic core with the carboxylic acid moiety wherein the carboxylic acid moiety is esterified with the at least one terminal hydroxyl group of the spacer portion or the branched dendritic core portion of the hybrid branched dendritic core.

A number of variations may include a process including providing at least one carboxylic acid moiety comprising from 6 to 40 carbon atoms; providing at least one spacer comprising at least one terminal hydroxyl group; reacting the spacer with the carboxylic acid moiety wherein the carboxylic acid moiety is esterified with the at least one terminal hydroxyl group of the spacer to form a hybrid carboxylic acid moiety; thereafter providing a branched dendritic core comprising greater than or equal to about 16 terminal hydroxyl groups; and reacting the branched dendritic core with the hybrid carboxylic acid moiety to provide at least one asphaltene dispersant/inhibitor.

Other illustrative variations within the scope of the invention will become apparent from the detailed description provided hereinafter. It should be understood that the detailed description and specific examples, while disclosing optional variations of the invention, are intended for purposes of illustration only and are not intended to limit the scope of the invention.

BRIEF DESCRIPTION OF THE DRAWINGS

Select examples of variations of the invention will become more fully understood from the detailed description and the accompanying drawings, wherein.

DETAILED DESCRIPTION OF ILLUSTRATIVE VARIATIONS

The following description of the variations is merely illustrative in nature and is in no way intended to limit the invention, its application, or uses. At the outset, it should be noted that in the development of any such actual embodiment, numerous implementation-specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possessed knowledge of the entire range and all points within the range.

Figure 1:
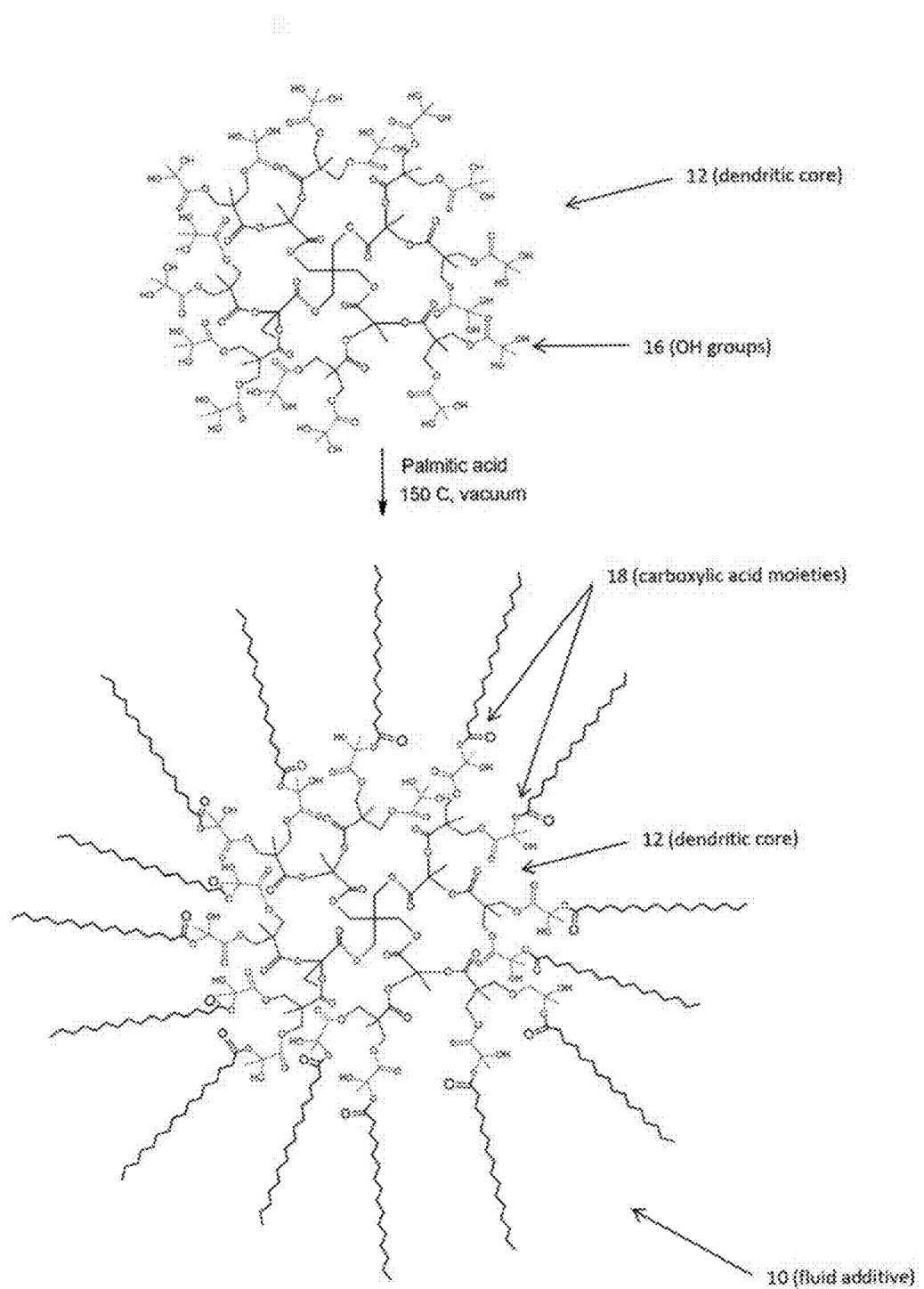
FIG. 1 is a schematic illustration of a fluid additive product and method of producing a fluid additive according to a number of variations.
Figure 2:
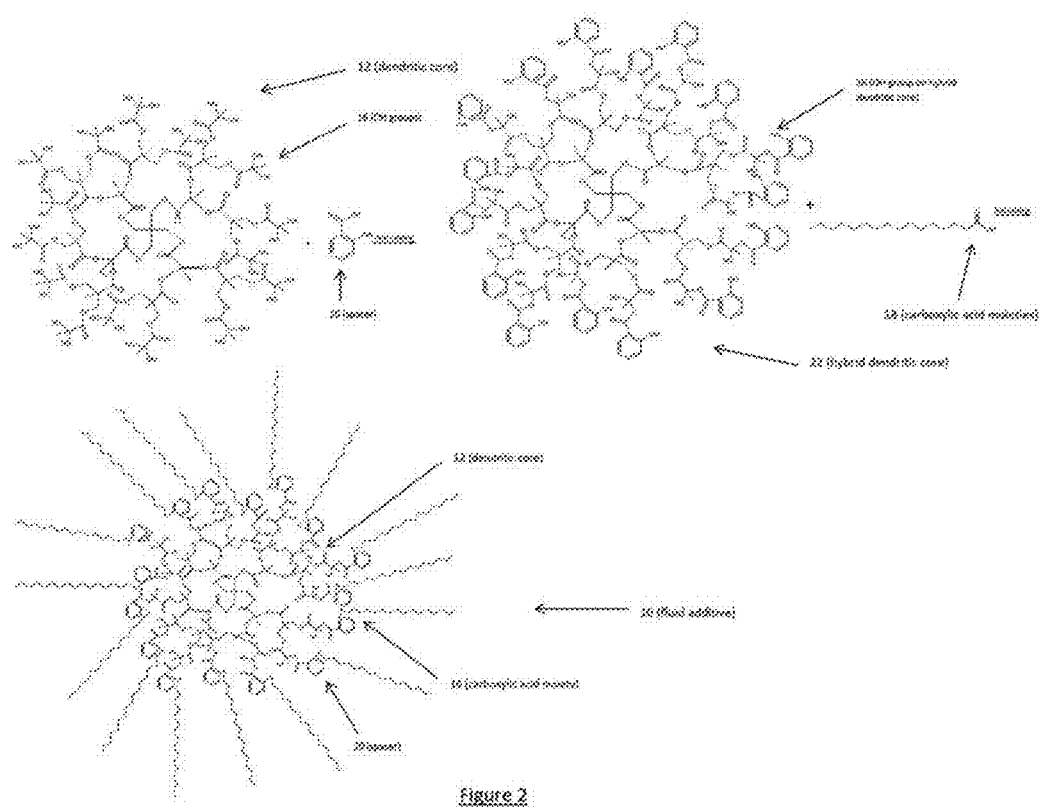
FIG. 2 is a schematic illustration of a fluid additive product and method of producing a fluid additive according to a number of variations.

FIG. 1 is a schematic illustration of a fluid additive product and method of producing a product according to a number of variations. A number of variations may include a fluid additive product 10. In a number of variations, the fluid additive 10 may be effective in dispersing and inhibiting asphaltene flocculation, precipitation, and/or growth in fluids, which may alleviate problems relating to flow assurance of the fluid. In a number of variations, the fluid may be a hydrocarbon fluid including, but not limited to, oil, crude oil condensate, middle distillate, fuel oil, diesel, kerosene, gasoline, various streams produced during extraction of hydrocarbons from wells, a combination thereof, or may be another type. A hydrocarbon fluid may be defined as a fluid comprising at least one hydrocarbon. In a number of variations, the fluid additive 10 may comprise a dendrimer. In a number of variations, the fluid additive 10 may comprise a dendrimer formed from convergent or divergent methods. Description of select illustrative dendrimers can be found in detail in Tomalia et al., Angew. Chem. Int. Ed. Engl, 29 (1990), 138; or in Khandekar et al., PCT Patent Application No: PCT/US2012/048786, included herein by reference thereto. In a number of variations, the dendrimer may be a branched dendrimer. In a number of variations, the fluid additive 10 may comprise a branched dendritic core 12. In a number of variations, the branched dendritic core 12 may comprise a first quaternary carbon center bonded to four second carbon atoms, wherein at least three of the four second carbon atoms may be bonded to a plurality of branched chain extender ligands 14. In a number of variations, the branched dendritic core has greater than or equal to 16 terminal hydroxyl groups. In a number of variations, at least one of the terminal hydroxyl groups of the branched dendritic core 12 may be esterified or otherwise reacted with at least one carboxylic acid moiety 18 comprising from 6 to 40 carbon atoms, or any range of carbon atoms between 6 and 40 carbon atoms, to produce a fluid additive 10. In a number of variations, at least one carboxylic acid moiety 18 may include unsaturated carboxylic acid moieties, saturated carboxylic acid moieties, branched carboxylic acid moieties, or linear carboxylic acid moieties or combinations thereof.

In a number of variations, at least one of the terminal hydroxyl groups of the branched dendritic core 12 may be esterified or otherwise reacted with at least one substituted carboxylic acid moiety 18 comprising from 6 to 40 carbon atoms to produce a fluid additive 10. In a number of variations, at least one of the terminal hydroxyl groups in the branched dendritic core 12 may be esterified or otherwise reacted with a combination of at least one carboxylic acid moiety 18 comprising from 6 to 40 carbon atoms (or any range of carbon atoms between 6 and 40 carbon atoms) and at least one substituted carboxylic acid moiety 18 comprising from 6 to 40 carbon atoms (or any range of carbon atoms between 6 and 40 carbon atoms) to product a fluid additive 10. In a number of variations, the substituted carboxylic acid moiety 18 comprises elements from Groups 13 to 17 of the Periodic Table of the elements. In a number of variations, reacting the branched dendritic core 12 with a carboxylic acid moiety in an esterification reaction can change the hydrophilic surface properties of the branched dendritic core 12 to lipophilic character in the resulting fluid additive 10. In a number of variations, reacting the branched dendritic core 12 with a carboxylic acid moiety 18 produces a fluid additive 10 with a surface modified with pendant long-chain alkane-groups and/or groups containing aromatic functionality.

In a number of variations the branched dendritic core 12 can be three dimensional highly branched molecules having a tree like structure. The branched dendritic core 12 may be highly symmetric or may hold an asymmetry. In a number of variations, the branched dendrimeric core 12 may comprise an initiator or nucleus having one or more reactive sites and a number of surrounding branching layers and optionally a layer of chain terminating molecules. The layers may be usually called generations, a designation hereinafter used. Branched dendritic or near dendritic macromolecules, or branched dendritic cores 12, may have three or more generations. A number of variations of the branched dendritic core 12 may be illustrated by Formulae (I) and (II),

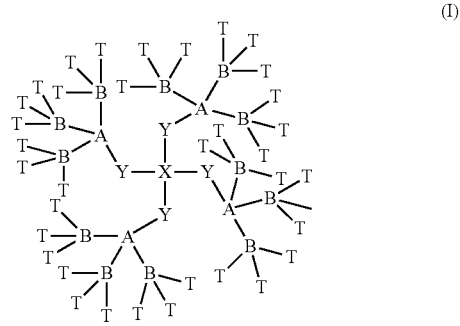

(I)

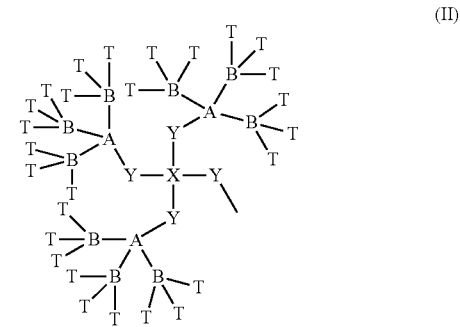

(II)

wherein X is a first quaternary carbon center bonded to four second carbon atoms Y, wherein each of the four second carbon atoms Y is each bonded through one or more chain extender ligands, which may be linear or branched, to produce the branched dendritic core. In a number of variations, A and B are chain extender ligands 14 having two or four reactive sites each. The chain extender ligands 14 may be polyfunctional ligands comprising hydroxyl groups, epoxides, carboxylic acids, or may be another type.

In a number of variations, each of the chain extender ligands 14 forms one generation in the branched dendritic core 12. As shown above, A and/or B may include a plurality of chain extenders, linked together, each providing a branching point which may be eventually terminated by a T functional group 16. Each of the A and B chain extenders may be the same or different.

In a number of variations, the branched dendrimer core 12, including the branches and terminating chains, may not include nitrogen atoms. In a number of variations, the branched dendrimer core 12, including the branches and terminating chains, consists essentially of carbon, hydrogen and oxygen. In a variation, A and B may consist essentially of carbon, hydrogen and/or oxygen. As disclosed above. T may be a terminating chain stopper functional group or terminal group 16 forming the last generation. In a number of variations, T may either be monofunctional or give a suitable terminal functionality. In a number of variations, T may be selected from at least one of a hydroxyl, carboxyl or epoxide group. In a number of variations, each T may be a terminal hydroxyl group or a terminal hydroxyl group esterified or otherwise reacted with at least one carboxylic acid moiety 18 comprising from 6 to 40 carbon atoms (or any range of carbon atoms between 6 and 40 carbon atoms). The branched dendritic core 12 may have greater than or equal to about 16 terminal hydroxyl groups, wherein at least one of the terminal hydroxyl groups 16 may be esterified or otherwise reacted with at least one carboxylic acid moiety 18 comprising from 6 to 40 carbon atoms (or any range of carbon atoms between 6 and 40 carbon atoms).

In a non-limiting variation, the branched dendritic core 12 may be represented by Formula III below.

(III)

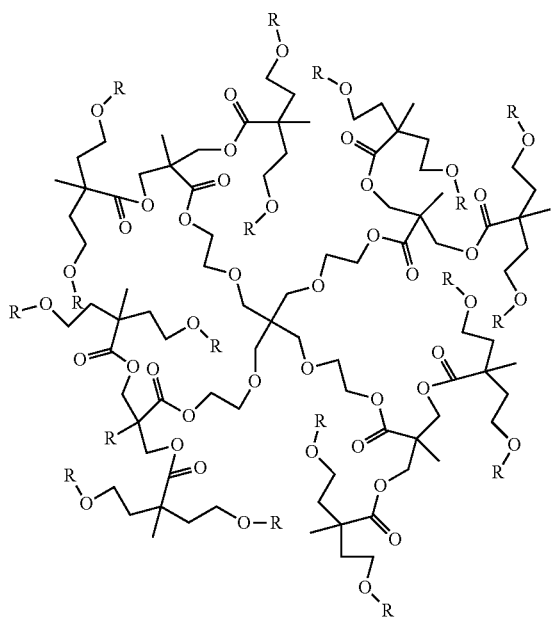

In a number of variations, the Formula III branched dendritic core 12 may not comprise a nitrogen functionality, and more specifically may not comprise amine or amide functionality. In a number of variations, each R may be a hydrogen (i.e., a hydroxyl terminal group) or an esterified hydroxyl group which has been esterified or otherwise reacted with at least one carboxylic acid moiety selected from the group consisting of: greater than or equal to about 6 carbon atoms, greater than or equal to about 10 carbon atoms, and from 6 to 40 carbon atoms (or any range of carbon atoms between 6 and 40 carbon atoms). Variations of R may include —COO—$(CH_2)_x$—$(CH)_y$—$CH_z$, wherein x+y=8-40, wherein y is from 0 to 5, and wherein z is 1, 2, or 3.

Accordingly, in a number of variations, the carboxylic acid moiety 18 may include unsaturated carboxylic acid moieties, saturated carboxylic acid moieties, branched carboxylic acid moieties, or linear carboxylic acid moieties or combinations thereof. In a number of variations, the carboxylic acid moiety 18 may have functional groups. In a number of variations, the carboxylic acid moiety 18 functional groups may cause the fluid additive 10 to be more hydrophilic or more hydrophobic. These functional groups may include, but are not limited to, aromatic (including, but not limited to, benzoic acid, naphthoic acid), hydroxyl, alkyl, alkenyl, alkynyl, phenyl, benzyl, halo, fluoro, chloro, bromo, iodo, carbonyl, aldehyde, haloformyl, carbonate ester, carboxylate, carboxyl, ester, methoxy, hydroperoxy, peroxy, ether, hemiacetal, acetal, hemiketal, ketal, orthoester, orthocarbonate ester, carboxamide, primary amine, secondary amine, ammonium ion, primary ketimine, secondary ketimine, primary aldimine, secondary aldimine, imide, azide, azo, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothioyl, carbonothioyl, phosphino, phosphono, phosphate, borono, boronate, borion, or boronate functional groups, or may be another type. These functional groups can be located anywhere within the carboxylic acid moiety 18 without impacting its terminal hydroxyl group 16. In a number of variations, the carboxylic acid moiety 18 may have heteroatoms. In a number of variations, the heteroatoms may be nitrogen, silicon, oxygen, sulfur, boron, chlorine, fluorine, or may be another type.

In a number of variations, prior to being esterified or otherwise reacted with the carboxylic acid moiety 18, the branched dendritic core 12 has a hydroxyl number of greater than or equal to about 490 mg KOH/g, wherein the hydroxyl number represents the hydroxyl content of a branched dendritic core 12, and may be derived by acetylating the hydroxyl and titrating the resultant acid against KOH, as is known in the art. The hydroxyl number may thus be the weight of KOH in milligrams that will neutralize the acid from 1 gram of the branched dendritic core 12 prior to being esterified or otherwise reacted with a carboxylic acid moiety 18.

In a number of variations, the branched dendritic core 12 may be esterified or otherwise reacted where at least one terminal hydroxyl group 16 of the branched dendritic core 12 may be esterified or otherwise reacted with at least one carboxylic acid 18 and/or substituted carboxylic acid moiety 18 having from 6 to 40 carbon atoms, or from 8 to 24 carbon atoms (or any range of carbon atoms between 6 and 40 carbon atoms). In a number of variations, the branched dendritic core 12 may be esterified or otherwise reacted where essentially all of the terminal hydroxyl groups of the branched dendritic core 12 may each be esterified or otherwise reacted with at least one carboxylic acid moiety 18 having from 12 to 22 carbon atoms (or any range of carbon atoms between 12 and 22 carbon atoms). In a number of variations, the terminal hydroxyl groups 16 on the branched dendritic core 12 may each be individually esterified or otherwise reacted with a corresponding number of the same carboxylic acid moiety 18. The carboxylic acid moiety 18 may be individually selected from a carboxylic acid moiety 18 and/or a substituted carboxylic acid moiety 18 having from 6 to 40 carbon atoms, or having from 12 to 22 carbon atoms (or any range of carbon atoms between 6 and 40 carbon atoms). In a number of variations, the carboxylic acid moieties 18 may comprise a fatty acid. In a number of variations, the carboxylic acid moieties 18 may be derived from carboxylic acids selected from the group consisting of substituted or unsubstituted capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, myristoleic acid, palmitoleic acid, sapienic acid, oleic acid, elaidic acid, vaccenic acid, linoleic acid, linoelaidic acid, a-linolenic acid, arachidonic acid, eicosapentaenoic acid, erucic acid, docosahexaenoic acid, resinolic acid, and combinations thereof in varying concentrations from 0-100%, or may be another type.

In a number of variations, the branched dendritic core 12 may be esterified or otherwise reacted with carboxylic acid moieties 18 selected from the group consisting of carboxylic acids and substituted carboxylic acids having from 8 to 24 carbon atoms, or having 12, 14, 16, 18, 20 and 22 carbon atoms, and combinations thereof. In a number of variations, the at least one carboxylic acid moiety 18 or substituted carboxylic acid moiety 18 may be selected from the group consisting of lauric acid, myristic acid, palmitic acid, stearic acid, 12-hydroxy steric acid, and combinations thereof.

In a number of variations, the carboxylic acid moiety 18 may be a substituted carboxylic acid moiety which may be substituted with at least one functional group comprising elements from one or more of Groups 13-17 of the Periodic Table of the elements. In a number of variations, the carboxylic acid moiety 18 may be a substituted carboxylic acid moiety which may be substituted with at least one functional group comprising elements from one or more of Group 13, 14, 15, 16, or 17 of the Periodic Table of the elements. In a number of variations, the at least one functional group consists essentially of, or may include, carbon, hydrogen, oxygen, sulfur and/or a halogen. In a number of variations, the substituted carboxylic acid moiety comprises a hydroxyl functional group, a halogen functional group, or a combination thereof. In a number of variations, the substituted carboxylic acid moiety may be a hydroxy substituted carboxylic acid. In a number of variations, the substituted carboxylic acid moiety may be 12 hydroxy stearic acid.

Commercially available branched dendritic cores 12, prior to esterification or other reaction, which may be suitable for use herein may include polyols sold by Perstorp AB Corporation Sweden under the name Boltorn®, (Perstorp, Sweden), including Boltorn® H20, Boltorn® H30, Boltorn® H40, and the like. A non-limiting variation of Boltorn® H20 synthesis is represented by Scheme 1 below. Table 1 below shows the Boltorn dendrimer specifications from Perstorp.

Scheme 1: Synthesis of Boltorn H20 from Pentaerythritol

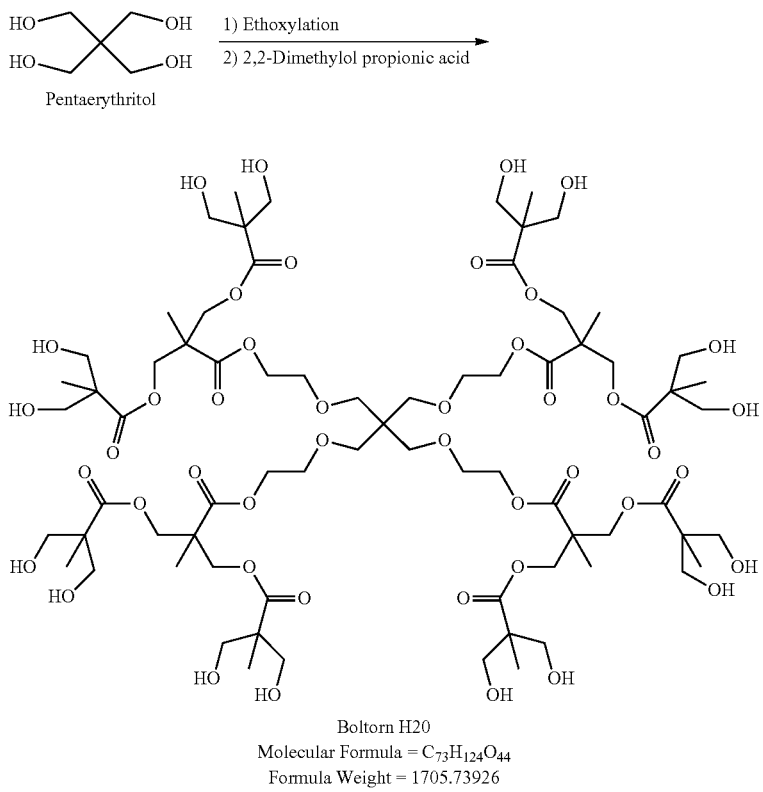

Boltorn H20
Molecular Formula = $C_{73}H_{124}O_{44}$
Formula Weight = 1705.73926

TABLE 1

| | | Boltorn dendrimers from Perstorp | | |
|---|---|---|---|---|
| Product | # Generations | # OH groups (theoretical) | MW (theoretical) | MW (nominal) |
| Boltorn H20 | 2 | 16 | 1705 | 1750 |
| Boltorn H30 | 3 | 32 | 3604 | 3500 |
| Boltorn H40 | 4 | 64 | 7316 | 5100 |
| Boltorn H311 | 3 | 23 | | 5700 |

In a number of variations, a branched dendritic core 12, such as those listed in Table 1, may be reacted with a carboxylic acid moiety 18. In a number of variations the carboxylic acid moiety 18 comprises a fatty acid. In a number of variations the reaction may be a standard Fischer esterification reaction. In a number of variations the branched dendritic core 12 may be mixed with the carboxylic acid moiety 18 with no solvent. In a number of variations there may be a 1 w/w % of an acid added. In some variations, the acid may be dodecylbenzene sulfonic acid (DDBSA). In a number of variations, water produced during the reaction may be removed by a vacuum. In a number of variations, the temperature of the reaction may be at a temperature of between 100-200° C. In a number of variations, the temperature of the reaction may be at a temperature of 150° C. In one non-limiting variation, Boltorn H30 may be reacted with palmitic acid (8 eq.) where the surface of the branched dendrimeric core 12 may be covered with 50% of the carboxylic acid moiety 18. The resulting product of this reaction may be a fluid additive 10 (Labeled Example 5). In a number of variations the fluid additive 10 may result with at least about 50% of the terminal hydroxyl groups 16 of the branched dendritic core 12 reacting with the carboxylic acid moiety 18. A synthesis of a non-limiting variation of a fluid additive 10 is shown in Scheme 2 below.

Scheme 2: Synthesis of Product Example 5

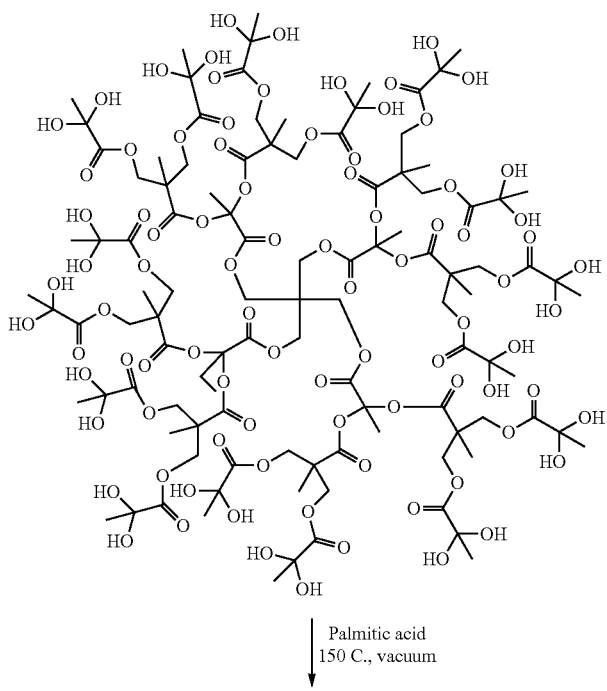

Palmitic acid
150 C., vacuum

-continued

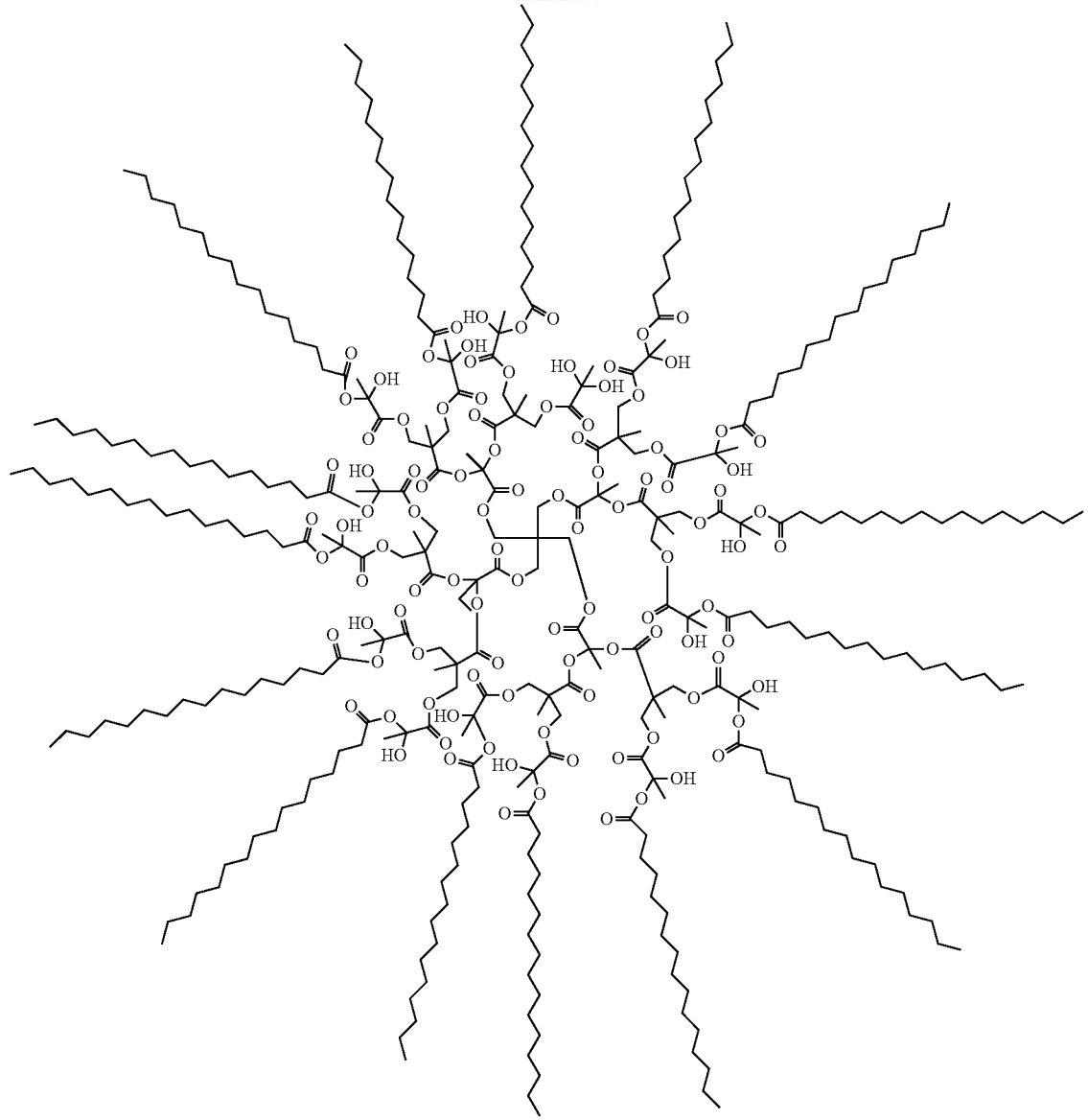

In a number of variations, the fluid additive 10 may include at least one spacer 20. In a number of variations the spacer 20 may an aromatic compound such as, but not limited to, salicylic acid, benzoic acid, naphthoic acid, or may be another type. In a number of variations, the spacer 20 may be reacted with at least one terminal hydroxyl group 16 on the branched dendritic core 12 to form a hybrid branched dendritic core 22. In a number of variations, a spacer 20 may be esterified or otherwise reacted with essentially all of the terminal hydroxyl groups 16 on the branched dendritic core 12 to form a hybrid branched dendritic core 22. In a number of variations, the terminal hydroxyl groups 16 on the branched dendritic core 12 may be each individually esterified or otherwise reacted with a corresponding number of individual spacers 20. In a number of variations, the spacer 20 may contain at least one terminal hydroxyl group 16. In a number of variations the spacer 20 and the branched dendritic core 12 may be esterified or otherwise reacted to form a hybrid branched dendritic core 22. In a number of variations, the reaction may be a Fischer esterification reaction. In a number of variations, the hybrid branched dendritic core 22 may be reacted with at least one carboxylic acid 18 and/or substituted carboxylic acid moiety 18 having from 6 to 40 carbon atoms, or from 8 to 24 carbon atoms, (or any range of carbon atoms between 6 and 40 carbon atoms) where at least one of the terminal hydroxyl groups 16 of the hybrid branched dendritic core 22 may be esterified or otherwise reacted with at least one carboxylic acid moiety 18 having from 6 to 40 carbon atoms, or from 8 to 24 carbon atoms (or any range of carbon atoms between 6 and 40 carbon atoms). In a number of variations, the reaction may be a Fischer esterification reaction. In a number of variations, the hybrid branched dendritic core 22 may be esterified or otherwise reacted with at least one carboxylic acid 18 and/or substituted carboxylic acid moiety 18 having from 6 to 40 carbon atoms, or from 8 to 24 carbon atoms (or any range of carbon atoms between 6 and 40 carbon atoms), where essentially all of the terminal hydroxyl groups 16 of the hybrid branched dendritic core 22 may each be esterified or otherwise reacted with at least one carboxylic acid moiety 18 having from 6 to 40 carbon atoms, or from 8 to 24 carbon atoms (or any range of carbon atoms between 6 and 40 carbon atoms). In a number of variations, the terminal hydroxyl groups 16 on the hybrid branched dendritic core 22 may be each individually esterified or otherwise reacted with a corresponding number of the same carboxylic acid moiety 18. All potential carboxylic acid moieties 18 listed above are understood to react with the terminal hydroxyl group 16 of the spacer 20 portion of the hybrid branched dendritic core 22 to form a fluid additive 10 in the same or a similar way as reacting with the terminal hydroxyl group on the branched dendritic core 12. In a number of variations, the carboxylic acid moiety 18 may be added to a solution and thereafter mixed with the spacer 20 before reaction of the spacer 20 with the branched dendritic core 12. In a number of variations, the carboyxlic acid moiety 18 may react with at least one terminal hydroxyl group 16 of the spacer 20 to form a hybrid carboxylic acid moiety 90. In a number of variations, a branched dendritic core 12 may be added to the hybrid carboxylic acid moiety 90 where the hybrid carboxylic acid moiety 90 may react with at least one terminal hydroxyl group 16 of the branched dendritic core 12 to form a fuel additive 10. In a number of variations, the branched dendritic core 12 may be added to a mixture of the spacer 20 and carboxylic acid moiety 18 to react to form the fuel additive 10.

In a number of variations, a branched dendritic core 12, such as those listed in Table 1, may be reacted with a spacer 20. In a number of variations the reaction may be a standard Fischer esterification reaction or condensation reaction. In a number of variations this reaction produces a hybrid branched dendritic core 22. In one non-limiting variation, Boltorn H30 (32 surface terminal hydroxyl groups 16 per molecule) may be reacted with salicylic acid (16 eq.) in the presence of a suitable acid catalyst to produce a hybrid branched dendritic core 20. In a number of variations, the acid catalyst may be dodecylbenzene sulfonic acid (DDBSA). In a number of variations the acid catalyst may be a lewis acid, a mineral acid, or an organic acid. Synthesis of a non-limiting variation of a hybrid branched dendritic core 22 is shown in Scheme 3 below.

In a number of variations, the hybrid branched dendritic core 22 may be reacted with a carboxylic acid moiety 18. In a number of variations, the carboxylic acid moiety 18 comprises a fatty acid. In a number of variations the reaction may be a standard Fischer esterification reaction. In a number of variations the hybrid branched dendritic core 22 may be mixed with the carboxylic acid moiety 18 with no solvent. In a number of variations there may be a 1 w/w % of an acid added. In a number of variations the acid may be a lewis acid, a mineral acid, or an organic acid. In some variations, the acid may be dodecylbenzene sulfonic acid (DBBSA). In a number of variations, water produced during the reaction may be removed by a vacuum (10-60 Torr). In a number of variations, the temperature of the reaction may be a temperature of between 100-200° C. In a number of variations, the temperature of the reaction may be at a temperature of 150° C. In one non-limiting variation, the hybrid branched dendritic core 22 product of Scheme 3 may be reacted with palmitic acid where the surface of the hybrid branched dendrimeric core 22 may be covered with 50% of the carboxylic acid moiety 18. The resulting product of this reaction may be a fluid additive 10. In a number of variations the fluid additive 10 may result with at least about 50% of the terminal hydroxyl groups 16 of the hybrid branched dendritic core 22 reacting with the carboxylic acid moiety 18. In a number of variations, the fluid additive 10 may be a waxy solid that melts around 30-50° C. In a number of variations the fluid additive 10 may be soluble in organic solvents. In a number of variations, the fluid additive 10 may be soluble in aromatic solvents. In a number of variations the fluid additive 10 may be insoluble in water. In a number of variations, the fluid additive 10 may be soluble or insoluble in methanol. A synthesis of a non-limiting variation of a fluid additive 10 is shown in Scheme 4 below. A range of different non-limiting carboxylic acid moieties 18, spacers 20, branched dendritic cores 12, and fluid additives 10 is provided in Table 2 below.

TABLE 2

Variations of Fluid Additives

| Fluid Additive | Boltorn core | Aromatic spacer | Fatty acid | Ratio (Dendrimer: spacer:fatty acid) |
| --- | --- | --- | --- | --- |
| Example I | H30 | None | Palmitic acid | 1:16 |
| Example II | H40 | 4-Hydroxybenzoic acid | Palmitic acid | 1:23:23 |
| Example III | H40 | 3-Hydroxybenzoic acid | Palmitic acid | 1:23:23 |
| Example IV | H40 | 3,5-Dihydroxy-benzoic acid | Palmitic acid | 1:26:46 |
| Example V | H30 | Salicylic acid | Palmitic acid | 1:16:8 |
| Example VI | H20 | 4-Aminobenzoic acid | Palmitic acid | 1:8:8 |
| Example VII | H30 | Hippuric acid | Palmitic acid | 1:16:16 |
| Example VIII | H30 | Gallic acid | Behenic acid | 1:16:16 |

In a number of variations, a mixture of several branched dendritic cores 12 (Table 1) may be reacted with a carboxylic acid moiety 18. In a number of variations, the carboxylic acid moiety 18 may be a fatty acid. In a number of variations, the fatty acid may be palmitic acid. The result of the reaction may be a fluid additive 10. In a number of variations the reaction may be a standard Fischer esterification reaction or a condensation reaction. A number of non-limiting variations of fluid additives 10 is shown in Table 3 below (Examples 1a-1e, 2a-2e, 3a-3e). In one non-limiting variation, a mixture of Boltorn H30 and Boltorn H40 may be mixed and reacted with palmitic acid to produce a fluid additive 10 (Example 1a). In one non-limiting variation, the reaction may be done in the presence of a suitable acid catalyst, such as, but not limited to, DDBSA, organic sulfonic acids, such as PTSA, or may be another suitable type. In one non-limiting variation, the reaction may be done at a temperature of between 100-200° C. In a number of variations, the temperature of the reaction may be at a temperature of 150° C. or greater. In one non-limiting variation, the reaction may be done under a vacuum.

TABLE 3

Selected Fluid Additives

| Fluid Additive | Boltorn cores | Fatty acid | Ratio (Dendrimers: fatty acid) |
| --- | --- | --- | --- |
| 1a | Boltorn H30 + Boltorn H40 | Palmitic acid | 1:1:39 |
| 1b | Boltorn H20 + Boltorn H30 | Palmitic acid | 1:1:24 |
| 1c | Boltorn H20 + Boltorn H40 | Palmitic acid | 1:1:31 |

TABLE 3-continued

Selected Fluid Additives

| Fluid Additive | Boltorn cores | Fatty acid | Ratio (Dendrimers: fatty acid) |
|---|---|---|---|
| 1d | Boltorn H20 + Boltorn H30 + Boltorn H40 | Palmitic acid | 1:1:1:47 |
| 1e | Boltorn H20 + Boltorn H30 + Boltorn H40 + Boltorn H311 | Palmitic acid | 1:1:1:1:63 |
| 2a | Boltorn H30 + Boltorn H40 | Stearic acid | 1:1:39 |
| 2b | Boltorn H20 + Boltorn H30 | Stearic acid | 1:1:24 |
| 2c | Boltorn H20 + Boltorn H40 | Stearic acid | 1:1:31 |
| 2d | Boltorn H20 + Boltorn H30 + Boltorn H40 | Stearic acid | 1:1:1:47 |
| 2e | Boltorn H20 + Boltorn H30 + Boltorn H40 + Boltorn H311 | Stearic acid | 1:1:1:1:63 |
| 3a | Boltorn H30 + Boltorn H40 | Behenic acid | 1:1:39 |
| 3b | Boltorn H20 + Boltorn H30 | Behenic acid | 1:1:24 |
| 3c | Boltorn H20 + Boltorn H40 | Behenic acid | 1:1:31 |
| 3d | Boltorn H20 + Boltorn H30 + Boltorn H40 | Behenic acid | 1:1:1:47 |
| 3e | Boltorn H20 + Boltorn H30 + Boltorn H40 + Boltorn H311 | Behenic acid | 1:1:1:1:63 |
| 4 | Boltorn H30 + Salicylic acid | Palmitic acid | 1:16:08 |
| 5 | Boltorn H30 | Palmitic acid | 1:16 |

In a number of variations, the fluid additive 10 comprises a branched dendritic core 12, which may be dissolved in a solvent. In a non-limiting variation, a 50 wt % of the fluid additive 10 dissolved in xylene has a viscosity as determined according to ASTM D2983 or an equivalent thereof. In a variation, the viscosity of a 50 wt % of the fluid additive 10 dissolved in xylene may be less than or equal to about 200 cp (centipoise) at 4° C., or less than or equal to about 100 cp at 4° C., or less than or equal to about 50 cp at 4° C., or less than or equal to about 25 cp at 4° C., or less than or equal to about 20 cp at 4° C., or less than or equal to about 15 cp at 4° C.

In a number of variations, a 25 wt % solution of the fluid additive 10 dissolved in xylene has a viscosity of less than or equal to about 100 cp at 4° C., or less than or equal to about 50 cp at 4° C., or less than or equal to about 40 cp at 40° C., or less than or equal to about 30 cp at 4° C., or less than or equal to about 20 cp at 4° C., or less than or equal to about 10 cp at 4° C.

In a number of variations, the fluid additive 10 may include one or more solvents and/or one or more surfactants, in addition to a dendrimer. Suitable solvents may include aromatic solvents, such as, without limitation, xylene and toluene. Suitable surfactants may include nonionic surfactants, cationic surfactant, and anionic surfactants. Variations of nonionic surfactants include, without limitation, ethoxylated linear alcohols, ethoxylated alkyl phenols, fatty acid esters, amine and amide derivatives, alkylpolyglucosides, ethleneoxide/propyleneoxide copolymers, polyalcohols, and ethoxylated polyalcohols. Variations of cationic surfactants include, without limitation, quaternary ammonium compounds, oxy and ethoxylated amines, linear diamines, amide, ester and ether-amines, alkanol amides, and amino acids.

Variations of anionic surfactants include, without limitation, alkyl ether sulfates, sulfated alkanolamides, gylceride sulfates, alky benzensulphonic acids and their salts, alpha olefin sulphonates, lignosulphonates, and phosphate esters. In a number of variations, a variation of a fluid additive 10 may be mixed with another variation of a fluid additive 10. For example, Fluid additive 1a may be mixed with fluid additive 1b to form a new fluid additive 10. In a number of variations, a variation of a fluid additive 10 may be mixed with other fluids such as production chemicals, other asphaltene dispersant/inhibitors, or may be mixed with another fluid.

In a number of variations, a fluid additive 10 may be put under an Asphaltene Dispersant Test to compare the asphaltene content of fluids and the ability of the fluid additive 10 to disperse and inhibit growth, aggregation, flocculation, and deposition of asphaltene in the fluid. In number of variations, a fluid additive 10 may be put under an Turbiscan™ Test to compare the asphaltene content of fluids and the ability of the fluid additive 10 to disperse and inhibit growth, aggregation, flocculation, and deposition of asphaltene in the fluid. A skilled artisan would understand the testing of fluid additives 10 for asphaltene but non-limiting testing methods can be found in ASTM method D7061 "Standard Test Method for Measuring n-Heptane Induced Phase Separation of Asphaltene-Containing Heavy Fuel Oils as Separability Number by an Optical Scanning Device."

Figure 3:
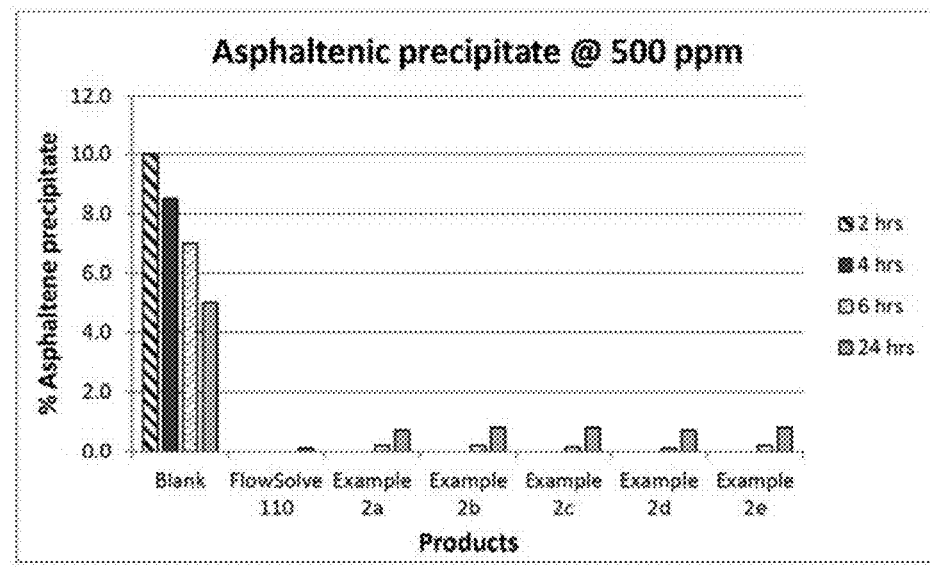
FIG. 3 is a bar graph comparing products vs. % asphaltene precipitate as a function of time for a number of fluid additives according to a number of variations.

FIG. 3 is a bar graph comparing products vs. % asphaltene precipitate as a function of time for a number of fluid additives according to a number of variations, such as some of those illustrated in Table 3. Commercially available product Flowsolve® 110 is used as a benchmark. FIG. 3 shows mixed dendritic cores+50% surface saturation with Palmitic acid (C16) as a carboxylic acid moiety 18.

Figure 4:
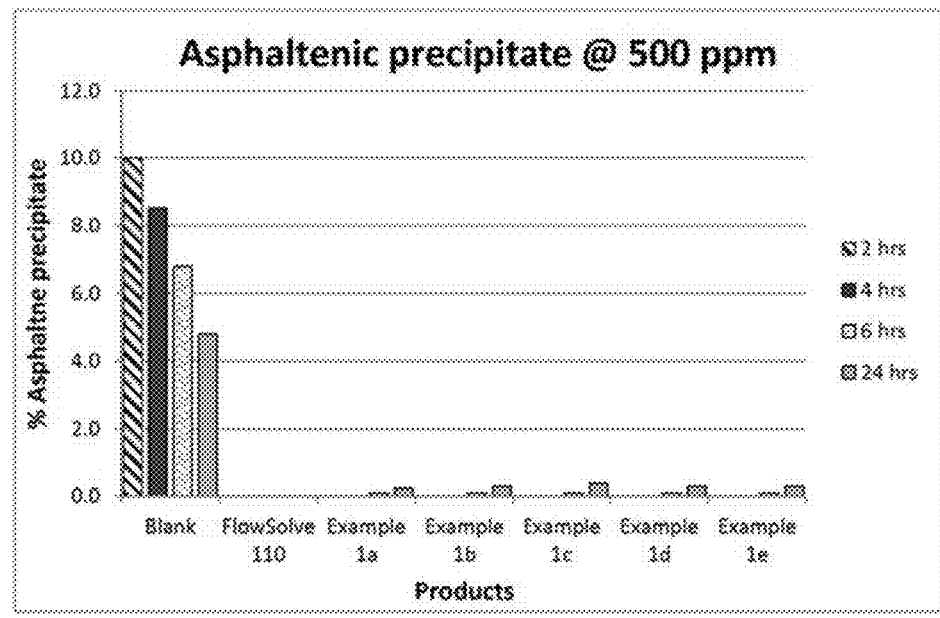
FIG. 4 is a bar graph comparing products vs. % asphaltene precipitate as a function of time for a number of fluid additives according to a number of variations.

FIG. 4 is a bar graph comparing products vs. % asphaltene precipitate as a function of time for a number of fluid additives according to a number of variations, such as some of those illustrated in Table 3. Commercially available product Flowsolve® 110 is used as a benchmark. FIG. 3 shows mixed dendritic cores+50% surface saturation with Stearic acid (C18) as a carboxylic acid moiety 18.

Figure 5:
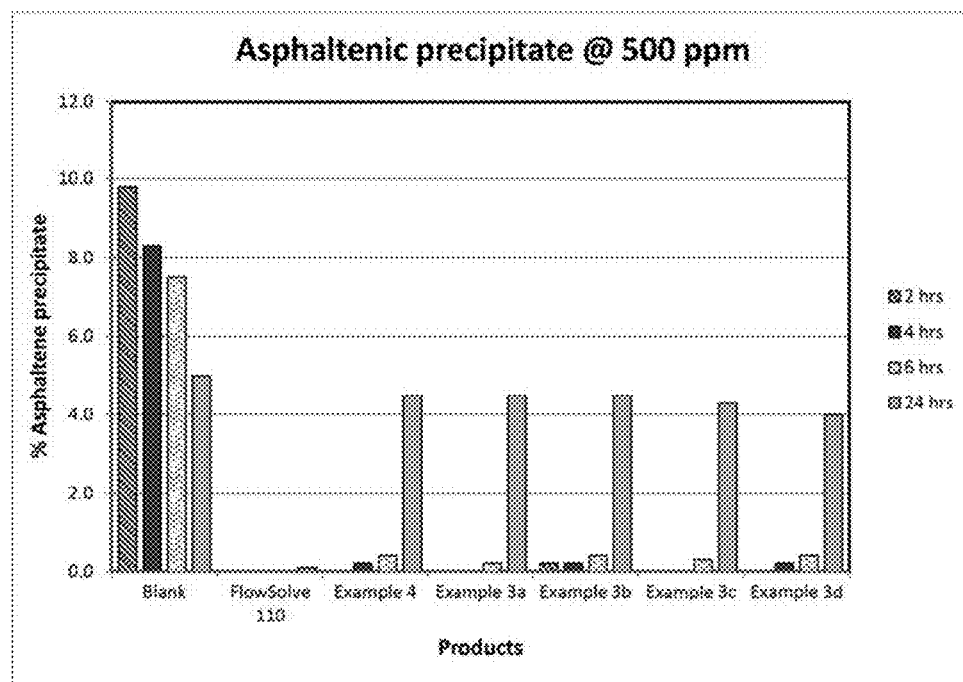
FIG. 5 is a bar graph comparing products vs. % asphaltene precipitate as a function of time for a number of fluid additives according to a number of variations.

FIG. 5 is a bar graph comparing products vs. % asphaltene precipitate as a function of time for a number of fluid additives according to a number of variations, such as some of those illustrated in Table 3. Commercially available product Flowsolve® 110 is used as a benchmark. FIG. 3 shows mixed dendritic cores+50% surface saturation with Behenic acid (C22) as a carboxylic acid moiety 18.

Figure 6:
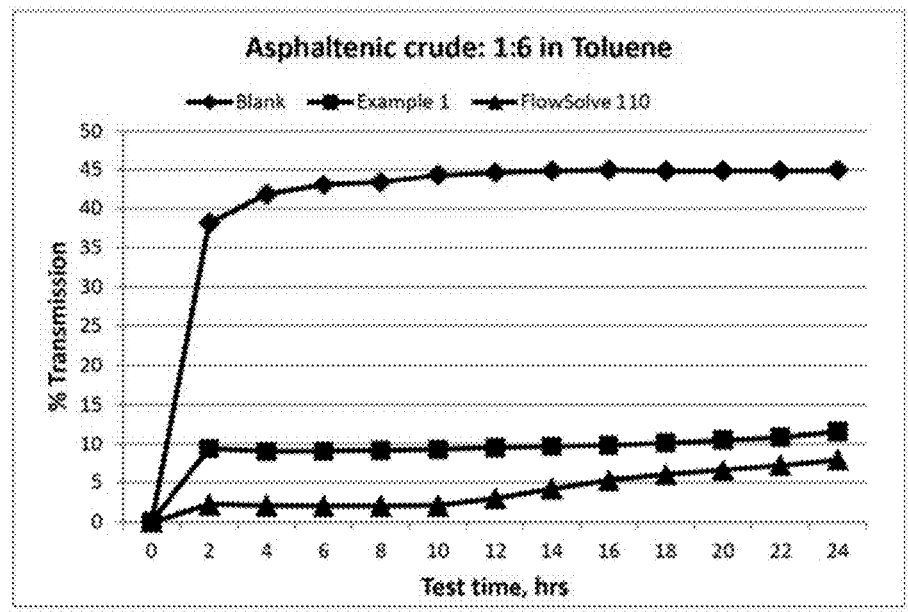
FIG. 6 is a table of Turbiscan™ test values and a line graph comparing test time vs. % transmission for a number of fluid additives according to a number of variations.

FIG. 6 is a table of Turbiscan™ test values and a line graph comparing test time vs. % transmission for a number of fluid additives according to a number of variations. Fluid additive 10 (Example 1a [example 1 in the graph]) in a fluid is compared with commercially available product Flowsolve® 110 in a fluid as well as a blank fluid.

The following description of variants is only illustrative of components, elements, acts, product and methods considered to be within the scope of the invention and are not in any way intended to limit such scope by what is specifically disclosed or not expressly set forth. The components, elements, acts, product and methods as described herein may be combined and rearranged other than as expressly described herein and still are considered to be within the scope of the invention.

Variation 1 may include a product including a fluid additive comprising at least one asphaltene dispersant/inhibitor comprising a branched dendritic core and at least one carboxylic acid moiety.

Variation 2 may include a product as set forth in claim 1 wherein the carboxylic acid moiety comprises from 6 to 40 carbon atoms.

Variation 3 may include a product as set forth in any of Variations 1-2 wherein the carboxylic acid moiety comprises a fatty acid.

Variation 4 may include a product as set forth in any of Variations 1-3 wherein the branched dendritic core comprises a first quaternary carbon center bonded to four second carbon atoms, wherein at least three of the four second carbon atoms are individually bonded to one or more chain extender ligands.

Variation 5 may include a product as set forth in Variation 1-4 wherein the branched dendritic core comprises greater than or equal to about 16 terminal hydroxyl groups.

Variation 6 may include a product as set forth in Variations 1-5 wherein the asphaltene dispersant/inhibitor further comprises at least one spacer esterified with at least one of the terminal hydroxyl groups of the branched dendritic core.

Variation 7 may include a product as set forth in Variation 6 wherein the spacer comprises at least one terminal hydroxyl group.

Variation 8 may include a product as set forth in any of Variation 5-7 wherein at least one carboxylic acid moiety is esterified with at least one of the terminal hydroxyl groups of the branched dendritic core or the spacer.

Variation 9 may include a product as set forth in any of Variations 6-8 wherein the spacer comprises salicylic acid.

Variation 10 may include a product as set forth in any of Variations 8-9 wherein carboxylic acid moieties are individually esterified with essentially all of the terminal hydroxyl groups of the branched dendritic core or the spacer.

Variation 11 may include a method including adding a fluid additive comprising at least one asphaltene dispersant/inhibitor comprising a branched dendritic core and a carboxylic acid to a first fluid to produce a second fluid, wherein the second fluid has a reduced percentage of asphaltene precipitation, flocculation, or deposition.

Variation 12 may include a method as set forth in Variation 11 wherein the fluid is a hydrocarbon fluid.

Variation 13 may include a process including providing a branched dendritic core comprising greater than or equal to about 16 terminal hydroxyl groups; providing at least one carboxylic acid moiety comprising from 6 to 40 carbon atoms; and reacting the branched dendritic core with the carboxylic acid moiety to provide a asphaltene dispersant/inhibitor.

Variation 14 may include a process as set forth in Variation 13 wherein the step of reacting the branched dendritic core with the carboxylic acid moiety to provide a asphaltene dispersant/inhibitor further comprises reacting the branched dendritic core with the carboxylic acid moiety wherein the carboxylic acid moiety is esterified with at least one of the terminal hydroxyl groups of the branched dendritic core.

Variation 15 may include a process as set forth in any of Variations 13-14 wherein the process further includes providing at least one spacer comprising at least one terminal hydroxyl group.

Variation 16 may include a process as set forth in Variation 15 wherein the step of reacting the branched dendritic core with the carboxylic acid moiety to provide a asphaltene dispersant/inhibitor further comprises reacting the branched dendritic core with the spacer wherein the spacer is esterified with at least one of the terminal hydroxyl groups of the branched dendritic core to produce a hybrid branched dendritic core; and thereafter reacting the hybrid branched dendritic core with the carboxylic acid moiety wherein the carboxylic acid moiety is esterified with the at least one terminal hydroxyl group of the spacer portion or the branched dendritic core portion of the hybrid branched dendritic core.

Variation 17 may include a process as set forth in Variations 15-16 wherein the spacer comprises salicylic acid.

Variation 18 may include a process as set forth in any of Variations 13-17: wherein the step of reacting the branched dendritic core with the carboxylic acid moiety to provide an asphaltene dispersant/inhibitor is done in the presence of an acid catalyst comprising at least one of a Lewis acid, a mineral acid, or an organic acid.

Variation 19 may include a process as set forth in any of Variations 13-18: wherein the step of reacting the branched dendritic core with the carboxylic acid moiety to provide an asphaltene dispersant/inhibitor further comprises applying a vacuum to remove water.

Variation 20 may include a process as set forth in any of Variations 13-19: wherein the step of reacting the branched dendritic core with the carboxylic acid moiety to provide a asphaltene dispersant/inhibitor takes place at a temperature between about 100 to about 200° C.

Variation 21 may include a method as set forth in any of Variations 11-12 wherein the hydrocarbon fluid comprises at least one of oil, crude oil condensate, middle distillate, fuel oil, diesel, kerosene, gasoline, various streams produced during extraction of hydrocarbons from wells, or a combination thereof.

Variation 22 may include a product as set forth in Variations 1-10 wherein the branched dendritic core is formed by convergent or divergent methods.

Variation 23 may include a process as set forth in Variations 13-20 wherein the branched dendritic core is formed by convergent or divergent methods.

Variation 24 may include a product as set forth in Variations 1-10 and 22 wherein each of the four second carbon atoms of the branched dendritic core is bonded to a plurality of branched chain extender ligands.

Variation 25 may include a product as set forth in Variations 1-10, 22 and 24 wherein the carboxylic acid moiety comprises a substituted carboxylic acid moiety.

Variation 26 may include a process as set forth in Variations 13-20 and 23 wherein the carboxylic acid moiety comprises a substituted carboxylic acid moiety.

Variation 27 may include a product as set forth in Variations 1-10, 22, and 24-25 wherein the branched dendritic core or hybrid branched dendritic core is esterified with a combination of at least one carboxylic acid moiety comprising from 6 to 40 carbon atoms, and at least one substituted carboxylic acid moiety comprising from 6 to 40 carbon atoms.

Variation 28 may include a process as set forth in Variations 13-20, 23, and 26 wherein the branched dendritic core or hybrid branched dendritic core is esterified with a combination of at least one carboxylic acid moiety comprising from 6 to 40 carbon atoms, and at least one substituted carboxylic acid moiety comprising from 6 to 40 carbon atoms.

Variation 29 may include a product as set forth in Variation 25 wherein the substituted carboxylic acid moiety 18 comprises elements from Groups 13 to 17 of the Periodic Table of the elements.

Variation 30 may include a process as set forth in Variation 26 wherein the substituted carboxylic acid moiety 18 comprises elements from Groups 13 to 17 of the Periodic Table of the elements.

Variation 31 may include a product as set forth in Variations 1-10, 22, 24-25, 27, and 29 wherein the branched dendritic core or hybrid branched dendritic core is esterified with a combination of at least one carboxylic acid moiety comprising from 6 to 40 carbon atoms, and at least one substituted carboxylic acid moiety comprising from 6 to 40 carbon atoms.

Variation 32 may include a process as set forth in Variations 13-20, 23, 25, and 40 wherein the branched dendritic core or hybrid branched dendritic core is esterified with a combination of at least one carboxylic acid moiety comprising from 6 to 40 carbon atoms, and at least one substituted carboxylic acid moiety comprising from 6 to 40 carbon atoms.

Variation 33 may include a product as set forth in Variations 1-10, 22, 24-25, 27, 29, and 31 wherein the branched dendritic core or hybrid branched dendritic core is asymmetric.

Variation 34 may include a process as set forth in Variations 13-20, 23, 25, 30, and 32 wherein the branched dendritic core or hybrid branched dendritic core is asymmetric.

Variation 35 may include a product as set forth in Variations 1-10, 22, 24-25, 27, 29, 31, and 33 wherein the dendritic core or hybrid branched dendritic core comprises chain extender ligands comprising at least one of hydroxyl groups, epoxies, or carboxylic acids.

Variation 36 may include a process as set forth in Variations 13-20, 23, 25, 30, 32, and 34 wherein the dendritic core or hybrid branched dendritic core comprises chain extender ligands comprising at least one of hydroxyl groups, epoxies, or carboxylic acids.

Variation 37 may include a product as set forth in Variations 1-10, 22, 24-25, 27, 29, 31, 33, and 35 wherein the dendritic core or hybrid branched dendritic core consists essential of carbon, hydrogen and oxygen.

Variation 38 may include a process as set forth in Variations 13-20, 23, 25, 30, 32, 34, and 36 wherein the dendritic core or hybrid branched dendritic core consists essential of carbon, hydrogen and oxygen.

Variation 39 may include a product as set forth in Variations 1-10, 22, 24-25, 27, 29, 31, 33, 35, and 37 wherein the dendritic core or hybrid branched dendritic core comprises at least one terminal group comprising at least one of a hydroxyl, carboxyl, or epoxide group.

Variation 40 may include a process as set forth in Variations 13-20, 23, 25, 30, 32, 34, 36, and 38 wherein the dendritic core or hybrid branched dendritic core comprises at least one terminal group comprising at least one of a hydroxyl, carboxyl, or epoxide group.

Variation 41 may include a product as set forth in Variations 1-10, 22, 24-25, 27, 29, 31, 33, 35, 37, and 39 wherein the dendritic core or hybrid branched dendritic core does not comprise a nitrogen functionality.

Variation 42 may include a process as set forth in Variations 13-20, 23, 25, 30, 32, 34, 36, 38, and 40 wherein the dendritic core or hybrid branched dendritic core does not comprise a nitrogen functionality.

Variation 43 may include a product as set forth in Variations 1-10, 22, 24-25, 27, 29, 31, 33, 35, 37, 39, and 41 wherein the carboxylic acid moiety comprises unsaturated carboxylic acid moieties, saturated carboxylic acid moieties, branched carboxylic acid moieties, or linear carboxylic acid moieties or combinations thereof.

Variation 44 may include a process as set forth in Variations 13-20, 23, 25, 30, 32, 34, 36, 38, 40, and 42 wherein the carboxylic acid moiety comprises unsaturated carboxylic acid moieties, saturated carboxylic acid moieties, branched carboxylic acid moieties, or linear carboxylic acid moieties or combinations thereof.

Variation 45 may include a product as set forth in Variations 1-10, 22, 24-25, 27, 29, 31, 33, 35, 37, 39, 41, and 43 wherein the carboxylic acid moiety comprises functional groups comprising at least one of aromatic, hydroxyl, alkyl, alkenyl, alkynyl, phenyl, benzyl, halo, fluoro, chloro, bromo, iodo, carbonyl, aldehyde, haloformyl, carbonate ester, carboxylate, carboxyl, ester, methoxy, hydroperoxy, peroxy, ether, hemiacetal, acetal, hemiketal, ketal, orthoester, orthocarbonate ester, carboxamide, primary amine, secondary amine, ammonium ion, primary ketimine, secondary ketimine, primary aldimine, secondary aldimine, imide, azide, azo, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothioyl, carbonothioyl, phosphino, phosphono, phosphate, borono, boronate, borion, or boronate functional groups.

Variation 46 may include a process as set forth in Variations 13-20, 23, 25, 30, 32, 34, 36, 38, 40, 42, and 44 wherein the carboxylic acid moiety comprises functional groups comprising at least one of aromatic, hydroxyl, alkyl, alkenyl, alkynyl, phenyl, benzyl, halo, fluoro, chloro, bromo, iodo, carbonyl, aldehyde, haloformyl, carbonate ester, carboxylate, carboxyl, ester, methoxy, hydroperoxy, peroxy, ether, hemiacetal, acetal, hemiketal, ketal, orthoester, orthocarbonate ester, carboxamide, primary amine, secondary amine, ammonium ion, primary ketimine, secondary ketimine, primary aldimine, secondary aldimine, imide, azide, azo, cyanate, isocyanate, nitrate, nitrile, isonitrile, nitrosooxy, nitro, nitroso, pyridyl, sulfhydryl, sulfide, disulfide, sulfinyl, sulfonyl, sulfino, sulfo, thiocyanate, isothiocyanate, carbonothioyl, carbonothioyl, phosphino, phosphono, phosphate, borono, boronate, borion, or boronate functional groups.

Variation 47 may include a product as set forth in Variations 1-10, 22, 24-25, 27, 29, 31, 33, 35, 37, 39, 41, 43, and 45 wherein the carboxylic acid moiety comprises heteroatoms comprising at least one of nitrogen, silicon, oxygen, sulfur, boron, chlorine, or fluorine.

Variation 48 may include a process as set forth in Variations 13-20, 23, 25, 30, 32, 34, 36, 38, 40, 42, 44, and 46 wherein the carboxylic acid moiety comprises heteroatoms comprising at least one of nitrogen, silicon, oxygen, sulfur, boron, chlorine, or fluorine.

Variation 49 may include a product as set forth in Variations 1-10, 22, 24-25, 27, 29, 31, 33, 35, 37, 39, 41, 43, 45, and 47 wherein the branched dendritic core has a hydroxyl number of greater than or equal to about 490 mg KOH/g.

Variation 50 may include a process as set forth in Variations 13-20, 23, 25, 30, 32, 34, 36, 38, 40, 42, 44, 46, and 48 wherein the branched dendritic core has a hydroxyl number of greater than or equal to about 490 mg KOH/g.

Variation 51 may include a product as set forth in Variations 1-10, 22, 24-25, 27, 29, 31, 33, 35, 37, 39, 41, 43, 45, 47, and 49 wherein the carboxylic acid moiety comprises at least one of substituted or unsubstituted capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, myristoleic acid, palmitoleic acid, sapienic acid, oleic acid, elaidic acid, vaccenic acid, linoleic acid, linoelaidic acid, a-linolenic acid, arachidonic acid, eicosapentaenoic acid, erucic acid, docosahexaenoic acid, resinolic acid, or combinations thereof in varying concentrations from 0-100%, 0.5-100% or any range of concentration between 0.5-100%.

Variation 52 may include a process as set forth in Variations 13-20, 23, 25, 30, 32, 34, 36, 38, 40, 42, 44, 46, 48, and 50 wherein the carboxylic acid moiety comprises at least one of substituted or unsubstituted capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, myristoleic acid, palmitoleic acid, sapienic acid, oleic acid, elaidic acid, vaccenic acid, linoleic acid, linoelaidic acid, a-linolenic acid, arachidonic acid, eicosapentaenoic acid, erucic acid, docosahexaenoic acid, resinolic acid, or combinations thereof in varying concentrations from 0-100%, 0.5-100% or any range of concentration between 0.5-100%.

Variation 53 may include a product as set forth in Variations 1-10, 22, 24-25, 27, 29, 31, 33, 35, 37, 39, 41, 43, 45, 47, 49, and 51 wherein at least 50% of the terminal hydroxyl groups of the branched dendritic core or hybrid branched dendritic core react with the carboxylic acid moiety.

Variation 54 may include a process as set forth in Variations 13-20, 23, 25, 30, 32, 34, 36, 38, 40, 42, 44, 46, 48, 50, and 52 wherein at least 50% of the terminal hydroxyl groups of the branched dendritic core or hybrid branched dendritic core react with the carboxylic acid moiety.

Variation 55 may include a product as set forth in Variations 1-10, 22, 24-25, 27, 29, 31, 33, 35, 37, 39, 41, 43, 45, 47, 49, 51, and 53 wherein a spacer is esterified with essentially all of the terminal hydroxyl groups of the branched dendritic core.

Variation 56 may include a process as set forth in Variations 13-20, 23, 25, 30, 32, 34, 36, 38, 40, 42, 44, 46, 48, 50, 52, and 54 wherein a spacer is esterified with essentially all of the terminal hydroxyl groups of the branched dendritic core.

Variation 57 may include a product as set forth in Variations 1-10, 22, 24-25, 27, 29, 31, 33, 35, 37, 39, 41, 43, 45, 47, 49, 51, 53, and 55 wherein the fluid additive is soluble in aromatic solvents but insoluble in water or methanol.

Variation 58 may include a process as set forth in Variations 13-20, 23, 25, 30, 32, 34, 36, 38, 40, 42, 44, 46, 48, 50, 52, 54, and 56 wherein the fluid additive is soluble in aromatic solvents but insoluble in water or methanol.

Variation 59 may include a process as set forth in Variations 13-20, 23, 25, 30, 32, 34, 36, 38, 40, 42, 44, 46, 48, 50, 52, 54, 56, and 58 wherein the acid catalyst is dodecylbenzene sulfonic acid.

Variation 60 may include a process as set forth in Variations 13-20, 23, 25, 30, 32, 34, 36, 38, 40, 42, 44, 46, 48, 50, 52, 54, 56, and 58-59 wherein no solvent is used.

Variation 61 may include a product as set forth in Variations 1-10, 22, 24-25, 27, 29, 31, 33, 35, 37, 39, 41, 43, 45, 47, 49, 51, 53, and 55 wherein the viscosity of a 50 wt % of the fluid additive dissolved in xylene is less than or equal to about 200 cp at 4° C.

Variation 62 may include a product as set forth in Variations 1-10, 22, 24-25, 27, 29, 31, 33, 35, 37, 39, 41, 43, 45, 47, 49, 51, 53, 55, and 61 wherein the viscosity of a 50 wt % of the fluid additive dissolved in xylene is less than or equal to about 100 cp at 4° C.

Variation 63 may include a product as set forth in Variations 1-10, 22, 24-25, 27, 29, 31, 33, 35, 37, 39, 41, 43, 45, 47, 49, 51, 53, 55, and 61-62 wherein the viscosity of a 50 wt % of the fluid additive dissolved in xylene is less than or equal to about 50 cp at 4° C.

Variation 64 may include a product as set forth in Variations 1-10, 22, 24-25, 27, 29, 31, 33, 35, 37, 39, 41, 43, 45, 47, 49, 51, 53, 55, and 61-63 the viscosity of a 50 wt % of the fluid additive dissolved in xylene is less than or equal to about 25 cp at 4° C.

Variation 65 may include a product as set forth in Variations 1-10, 22, 24-25, 27, 29, 31, 33, 35, 37, 39, 41, 43, 45, 47, 49, 51, 53, 55, and 61-64 wherein the viscosity of a 50 wt % of the fluid additive dissolved in xylene is less than or equal to about 20 cp at 4° C.

Variation 66 may include a product as set forth in Variations 1-10, 22, 24-25, 27, 29, 31, 33, 35, 37, 39, 41, 43, 45, 47, 49, 51, 53, 55, and 61-65 the viscosity of a 50 wt % of the fluid additive dissolved in xylene is less than or equal to about 15 cp at 4° C.

Variation 67 may include a product as set forth in Variations 1-10, 22, 24-25, 27, 29, 31, 33, 35, 37, 39, 41, 43, 45, 47, 49, 51, 53, 55, and 61-66 wherein the viscosity of a 25 wt % of the fluid additive dissolved in xylene is less than or equal to about 100 cp at 4° C.

Variation 68 may include a product as set forth in Variations 1-10, 22, 24-25, 27, 29, 31, 33, 35, 37, 39, 41, 43, 45, 47, 49, 51, 53, 55, and 61-67 wherein the viscosity of a 25 wt % of the fluid additive dissolved in xylene is less than or equal to about 50 cp at 4° C.

Variation 69 may include a product as set forth in Variations 1-10, 22, 24-25, 27, 29, 31, 33, 35, 37, 39, 41, 43, 45, 47, 49, 51, 53, 55, and 61-68 wherein the viscosity of a 25 wt % of the fluid additive dissolved in xylene is less than or equal to about 40 cp at 4° C.

Variation 70 may include a product as set forth in Variations 1-10, 22, 24-25, 27, 29, 31, 33, 35, 37, 39, 41, 43, 45, 47, 49, 51, 53, 55, and 61-69 the viscosity of a 25 wt % of the fluid additive dissolved in xylene is less than or equal to about 30 cp at 4° C.

Variation 71 may include a product as set forth in Variations 1-10, 22, 24-25, 27, 29, 31, 33, 35, 37, 39, 41, 43, 45, 47, 49, 51, 53, 55, and 61-70 wherein the viscosity of a 25 wt % of the fluid additive dissolved in xylene is less than or equal to about 20 cp at 4° C.

Variation 72 may include a product as set forth in Variations 1-10, 22, 24-25, 27, 29, 31, 33, 35, 37, 39, 41, 43, 45, 47, 49, 51, 53, 55, and 61-71 wherein the viscosity of a 25 wt % of the fluid additive dissolved in xylene is less than or equal to about 10 cp at 4° C.

Variation 73 may include a product as set forth in Variations 1-10, 22, 24-25, 27, 29, 31, 33, 35, 37, 39, 41, 43, 45, 47, 49, 51, 53, 55, and 61-72 wherein the product is soluble in organic solvents.

Variation 74 may include a product as set forth in Variations 1-10, 22, 24-25, 27, 29, 31, 33, 35, 37, 39, 41, 43, 45, 47, 49, 51, 53, 55, and 61-73 wherein the product is soluble in methanol.

Variation 74 may include a process including: providing at least one carboxylic acid moiety comprising from 6 to 40 carbon atoms; providing at least one spacer comprising at least one terminal hydroxyl group; reacting the spacer with the carboxylic acid moiety wherein the carboxylic acid moiety is esterified with the at least one terminal hydroxyl group of the spacer to form a hybrid carboxylic acid moiety; thereafter providing a branched dendritic core comprising greater than or equal to about 16 terminal hydroxyl groups; and reacting the branched dendritic core with the hybrid carboxylic acid moiety to provide at least one asphaltene dispersant/inhibitor.

The above description of select examples of the invention is merely exemplary in nature and, thus, variations or variants thereof are not to be regarded as a departure from the spirit and scope of the invention.

What is claimed is:

1. A product comprising:
   an organic solvent; and
   a fluid additive comprising at least one asphaltene dispersant/inhibitor comprising:
   a reaction product of a branched dendritic core lacking a nitrogen functional group and at least one carboxylic acid moiety; and
   at least one aromatic spacer between the branched dendritic core and the at least one carboxylic acid moiety, wherein the aromatic spacer is derived from a monohydroxy aromatic carboxylic acid or a monoamino aromatic carboxylic acid,
   wherein the fluid additive is solublized in the organic solvent.

2. The product of claim 1 wherein the carboxylic acid moiety comprises from 6 to 40 carbon atoms.

3. The product of claim 1 wherein the carboxylic acid moiety comprises a fatty acid.

4. The product of claim 1 wherein the branched dendritic core comprises a first quaternary carbon center bonded to four second carbon atoms, wherein at least three of the four second carbon atoms are individually bonded to one or more chain extender ligands having two or four reactive sites.

5. The product of claim 4 wherein the branched dendritic core comprises greater than or equal to about 16 terminal hydroxyl groups.

6. The product of claim 5 wherein the at least one aromatic spacer is esterified with at least one of the terminal hydroxyl groups of the branched dendritic core.

7. The product of claim 1 wherein the aromatic spacer comprises salicylic acid.

8. The product of claim 6 wherein the carboxylic acid moieties are individually esterified with at least one of the terminal hydroxyl groups of the branched dendritic core or the aromatic spacer.

9. A method comprising adding the product of claim 1 to a first fluid containing asphaltenes to produce a second fluid, wherein the second fluid has a reduced percentage of asphaltene precipitation, flocculation, or deposition.

10. The method of claim 9 wherein the first fluid is a hydrocarbon fluid.

11. A process comprising:
    providing a branched dendritic core comprising greater than or equal to about 16 terminal hydroxyl groups reacted with at least one aromatic spacer, wherein the aromatic spacer is derived from a monohydroxy aromatic carboxylic acid or a monoamino aromatic carboxylic acid;
    providing at least one carboxylic acid moiety comprising from 6 to 40 carbon atoms; and,
    reacting the branched dendritic core with the carboxylic acid moiety to provide an asphaltene dispersant/inhibitor.

12. The process of claim 11 wherein the reacting the branched dendritic core with the carboxylic acid moiety to provide an asphaltene dispersant/inhibitor further comprises reacting the branched dendritic core with the carboxylic acid moiety wherein the carboxylic acid moiety is esterified with at least one of the terminal hydroxyl groups of the branched dendritic core.

13. The process of claim 11 wherein the step of reacting the branched dendritic core with the carboxylic acid moiety to provide an asphaltene dispersant/inhibitor further comprises reacting the branched dendritic core with the aromatic spacer wherein the aromatic spacer is esterified with at least one of the terminal hydroxyl groups of the branched dendritic core to produce a hybrid branched dendritic core; and thereafter reacting the hybrid branched dendritic core with the carboxylic acid moiety wherein the carboxylic acid moiety is esterified with the at least one terminal hydroxyl group of the spacer portion or the branched dendritic core portion of the hybrid branched dendritic core.

14. The process of claim 11 wherein the aromatic spacer comprises salicylic acid.

15. The process of claim 11 wherein the step of reacting the branched dendritic core with the carboxylic acid moiety to provide an asphaltene dispersant/inhibitor is conducted in the presence of an acid catalyst.

16. The process of claim 11 wherein the step of reacting the branched dendritic core with the carboxylic acid moiety to provide an asphaltene dispersant/inhibitor further comprises applying a vacuum to remove water.

17. A process comprising:
    providing at least one carboxylic acid moiety comprising from 6 to 40 carbon atoms;
    providing at least one aromatic spacer comprising at least one terminal hydroxyl group;
    reacting the spacer with the carboxylic acid moiety wherein the carboxylic acid moiety is esterified with the at least one terminal hydroxyl group of the spacer to form a hybrid carboxylic acid moiety;
    thereafter providing a branched dendritic core comprising greater than or equal to about 16 terminal hydroxyl groups; and
    reacting the branched dendritic core with at least one of the hybrid carboxylic acid moiety to provide an asphaltene dispersant/inhibitor.

* * * * *